(12) United States Patent
Eldred et al.

(10) Patent No.: US 6,360,621 B1
(45) Date of Patent: Mar. 26, 2002

(54) ENVIRONMENTAL TESTING CHAMBER

(75) Inventors: John Eldred; Christopher Scholten, both of Holland; Vincent Jasinski, Grand Rapids; Randall Beekman, Dorr; Clinton Peterson, Holland; Kevin Ewing, Holland; Roger Lubbers, Holland, all of MI (US)

(73) Assignee: Venturedyne, Ltd., Milwaukee, WI (US)

( * ) Notice: Subject to any disclaimer, the term of this patent is extended or adjusted under 35 U.S.C. 154(b) by 0 days.

(21) Appl. No.: 09/344,465

(22) Filed: Jun. 25, 1999

(51) Int. Cl.[7] ............................................. G01N 29/04
(52) U.S. Cl. ....................................................... 73/865.6
(58) Field of Search ............................. 73/865.8, 865.6; 374/45, 57; 379/1; 455/115

(56) References Cited

U.S. PATENT DOCUMENTS

| | | | |
|---|---|---|---|
| 4,860,602 A | * | 8/1989 | Hines et al. ................ 73/865.6 |
| 5,423,072 A | * | 6/1995 | Iwashita et al. |
| 5,513,538 A | * | 5/1996 | Baker et al. ................ 73/865.6 |
| 5,540,109 A | * | 7/1996 | Hobbs ........................ 73/865.6 |
| 5,613,776 A | * | 3/1997 | Turner et al. |
| 5,805,667 A | * | 9/1998 | Alvarez et al. |
| 5,915,838 A | * | 6/1999 | Stals et al. |
| 6,097,001 A | * | 8/2000 | Richardson et al. |

* cited by examiner

*Primary Examiner*—Robert Raevis
(74) *Attorney, Agent, or Firm*—Jansson, Shupe & Munger, Ltd.

(57) ABSTRACT

An apparatus is provided for conducting environmental tests on a device. The apparatus includes a cabinet defining a testing chamber for receiving the device therein. Control structure, operatively connected to the cabinet, varies the environmental conditions within the testing chamber to a user desired environment. An isolation structure is provided for isolating the device within the testing chamber and preventing electromagnetic and radio frequency waves from passing therethrough.

21 Claims, 14 Drawing Sheets

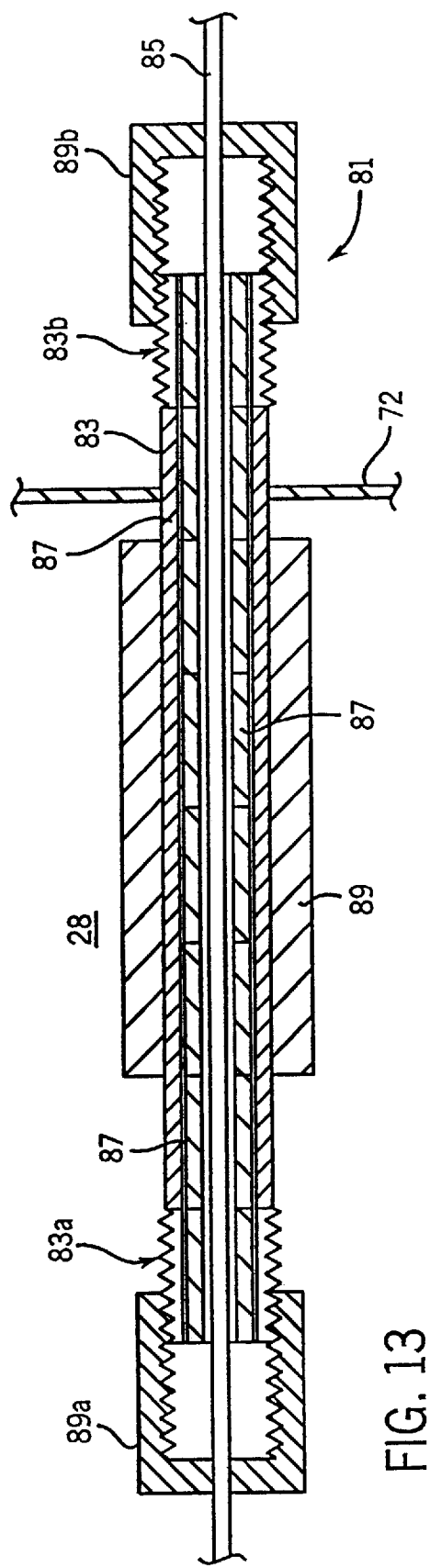
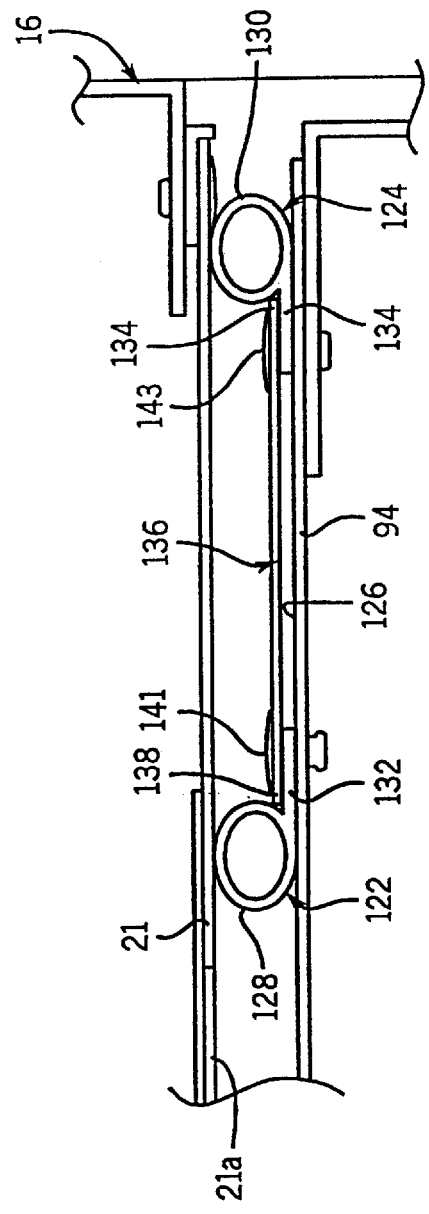
FIG. 13
FIG. 12

ENVIRONMENTAL TESTING CHAMBER

FIELD OF THE INVENTION

This invention relates generally to environmentally controlled testing chambers, and in particular, to an environmentally controlled testing chamber which incorporates electromagnetic and radio frequency wave shielding of the interior thereof.

BACKGROUND OF THE INVENTION

Many types of electronic and wireless devices undergo testing to improve the overall quality and reliability of the devices. Typically, these types of electronic and wireless devices undergo a series of environmental tests under various combinations of temperature, humidity, and other climatic conditions to insure product reliability and performance at extreme environmental conditions. Further, many of such devices are tested to insure that the devices are not adversely affected when a plurality of such devices are used in a common environment.

In order to test their electronic and wireless devices, manufactures often utilize environmental testing chambers which are capable of producing rapid and extreme changes in temperature, humidity and other climatic conditions. A prominent designer and manufacture of such environmental testing chambers is Thermotron Industries, Inc., of Holland, Mich.

The climatic conditions within the environmental testing chamber are controlled by heating, humidity and air conditioning units which generate the rapid changes in climatic conditions within the test chamber. However, these units could possibly generate electromagnetic and radio frequency waves which may adversely affect the testing of the electronic and wireless devices in the environmental testing chamber. Likewise, many electronic and wireless devices generate their own electromagnetic and radio frequency waves during operation and/or testing. Due to the large number of devices which are tested simultaneously in the environmental testing chamber, individuals in proximity to the environmental testing chamber may be exposed to the cumulative electromagnetic and radio frequency waves generated by the devices.

Heretofore, in order to minimise the effects of the electromagnetic and radio frequency waves emanating from an environmental testing chamber during testing of electronic and wireless devices, a screened enclosure is built around the entire environmental testing chamber in order to isolate the testing chamber from the surrounding environment. Not only does such an enclosure occupy a substantial amount of floor space in the testing facility, but also traps heat generated by the test chamber therein. This, in turn, may result in a uncomfortable working environment for the operators conducting the desired testing and increases the stress on the equipment within the screened enclosure.

Therefore, it is a primary object and feature of the present invention to provide an environmental testing chamber for testing products under various climatic conditions.

It is a further object and feature of the present invention to provide an environmental testing chamber which limits electromagnetic and radio frequency waves from entering and/or exiting the interior cavity of the environmental testing chamber.

It is a still further object and feature of the present invention to provide an environmental testing chamber which is simple and less expensive to manufacture.

It is a still further object and feature of the present invention to provide an environmental test chamber which reduces the effects of electromagnetic and radio frequency waves emanating therefrom during the testing of electronic and wireless devices.

SUMMARY OF THE INVENTION

In accordance with the present invention, an apparatus is provided for conducting environmental tests on a device. The apparatus includes a cabinet defining a testing chamber for receiving the device therein. A control structure is interconnected the cabinet for varying environmental conditions within the testing chamber to a user desired environment. Isolation structure provides a barrier between the device and the control structure.

The isolation structure may include an enclosure which surrounds the device. The enclosure is receivable within the testing chamber and is formed from electromagnetic wave absorbing material and/or a radio wave absorbing material. The enclosure includes a plurality of openings therein so as to allow for the flow of air therethrough.

Alternatively, it is contemplated that the isolation structure include a shield positioned between the control structure and the device. The shield may be formed from an electromagnetic wave absorbing and/or a radio wave absorbing material. Openings are provided in the shield to allow for the flow of air therethrough.

A thermocouple extends into the testing chamber for monitoring the temperature therein. The thermocouple is partially surrounded by an isolation tube to limit any electromagnetic and/or radio frequency waves radiating from the thermocouple from entering the testing chamber. The isolation tube of the thermocouple includes a first layer for preventing electromagnetic waves from passing therethrough and a second outer layer. It is contemplated the inner layer be formed from plurality of ferrite sections.

In accordance with a still further aspect of the present invention, an apparatus is provided for conducting an environmental test on a device. The apparatus includes a cabinet which defines a testing chamber for receiving the device therein. A door is pivotably mounted to the cabinet and movable between a first open position allowing access to the interior of the testing chamber and a second closed position wherein access to the testing chamber is prevented. Door sealing structure is provided for sealing the intersection of the door and the cabinet when the door is in the closed position. Control structure operatively connected to the cabinet varies the environmental conditions within the testing chamber to a user desired environment. An isolation structure isolates the device from the control structure by limiting predetermined waves from passing therethrough.

It is contemplated that the isolation structure include a shield positioned within the testing chamber between the control structure and the device. It is contemplated for the shield to surround the entire device. The shield is formed from a electromagnetic wave absorbing material and/or a radio wave absorbing material. A plurality of passages arranged in a honeycomb configuration in the shield allow for the flow of air therethrough. A sealing structure is provided about the outer periphery of the shield so as to prevent electromagnetic and radio frequency waves from traveling therepast.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings:

FIG. 12 is an enlarged, sectional view taken along line 12—12 of FIG. 9;

FIG. 13 is a cross-sectional view showing a thermocouple for use with the environmental testing chamber of the present invention;

DETAILED DESCRIPTION OF THE DRAWINGS

Figure 1:
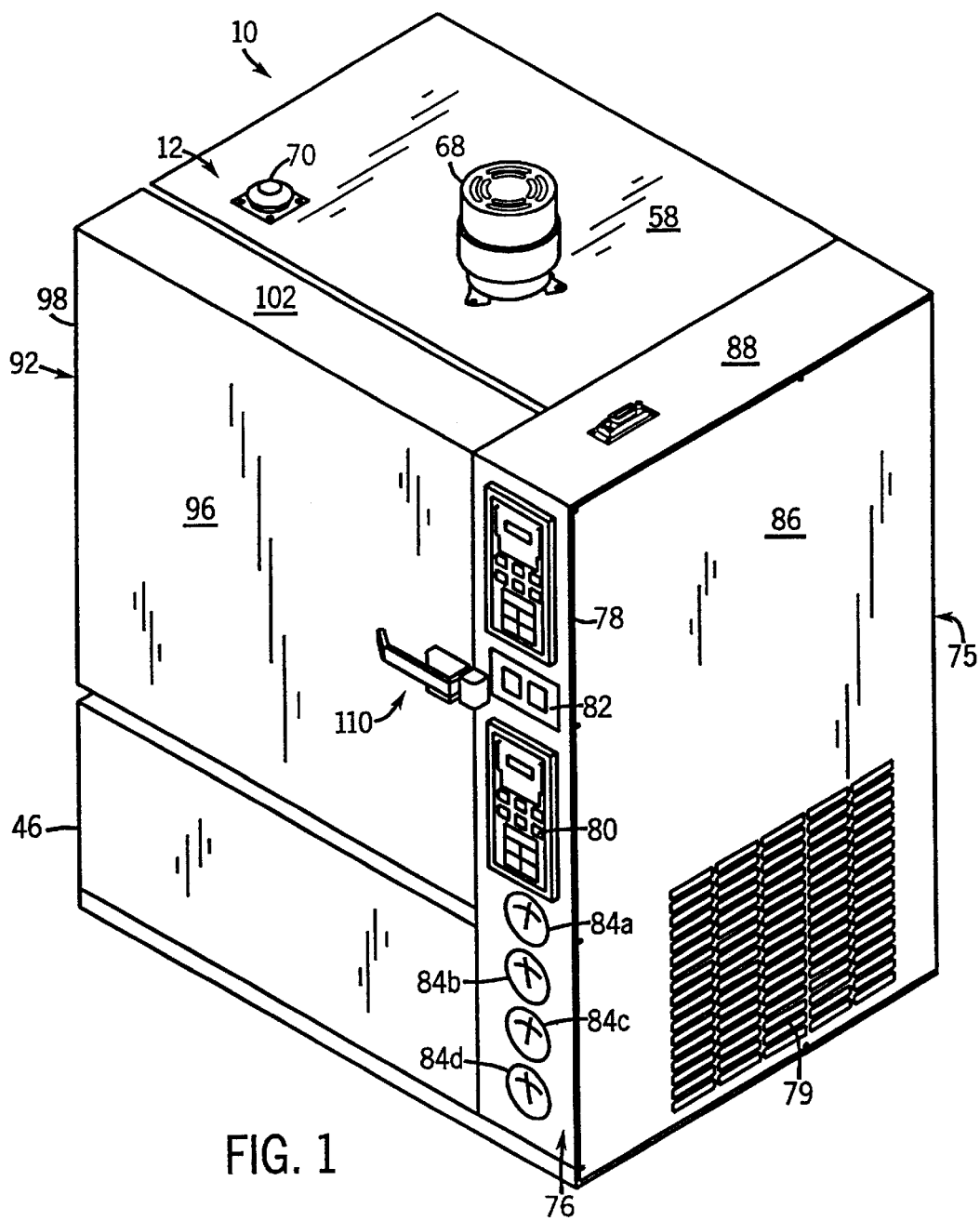
FIG. 1 is a front, isometric view of an environmental testing chamber in accordance with the present invention.
Figure 2:
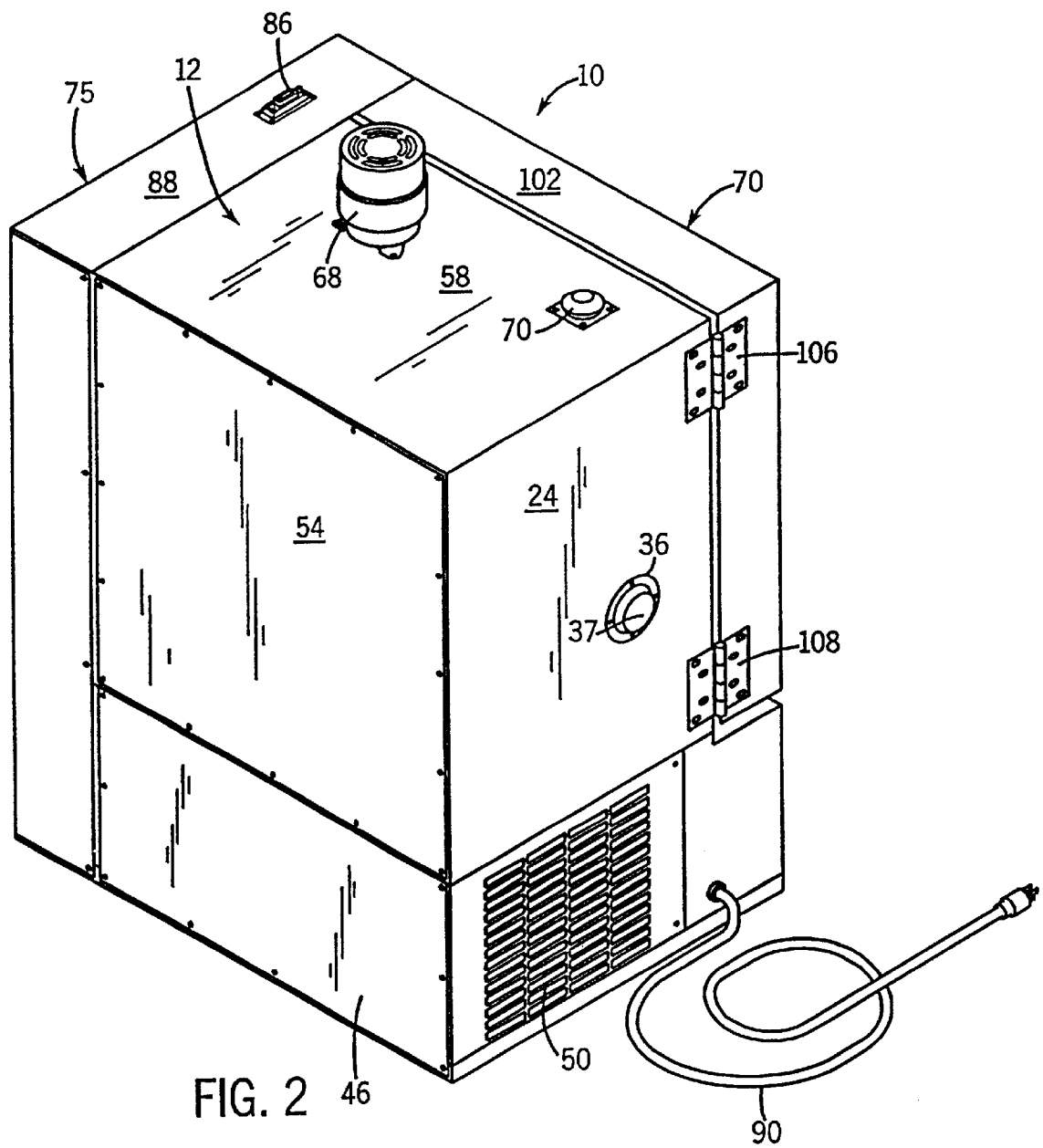
FIG. 2 is a rear, isometric view of the environmental testing chamber of FIG. 1.

Referring to FIGS. 1–4, an environmental testing chamber in accordance with the present invention is generally designated by the reference numeral 10. Environmental testing chamber 10 includes a body portion 12 defined by sidewalls 14 and 16, upper and lower walls 18 and 20, respectively, and rear wall 22. A face plate 21 having an opening 23 therein is mounted to the forward end of sidewalls 14 and 16, upper wall 18 and lower wall 20. Opening 23 in face plate 21 is in communication with interior cavity 28 in body portion 12 defined by sidewalls 14 and 16, upper wall 18 and lower wall 20. Interior cavity 28 in body portion 12 is provided for receiving products 25, FIGS. 15–16, therein to be tested.

Sidewall 14 is defined by an inner panel 22 and an outer panel 24 having insulation disposed therebetween. It is contemplated that inner and outer panels 22 and 24, respectively, be formed from an electromagnetic and radio frequency wave absorbing material. An access port 26 extends through sidewall 14 in order to allow an operator of environmental testing chamber 10 to insert wiring, cabling of the like into interior cavity 28 of environmental testing chamber 10.

Figure 14:
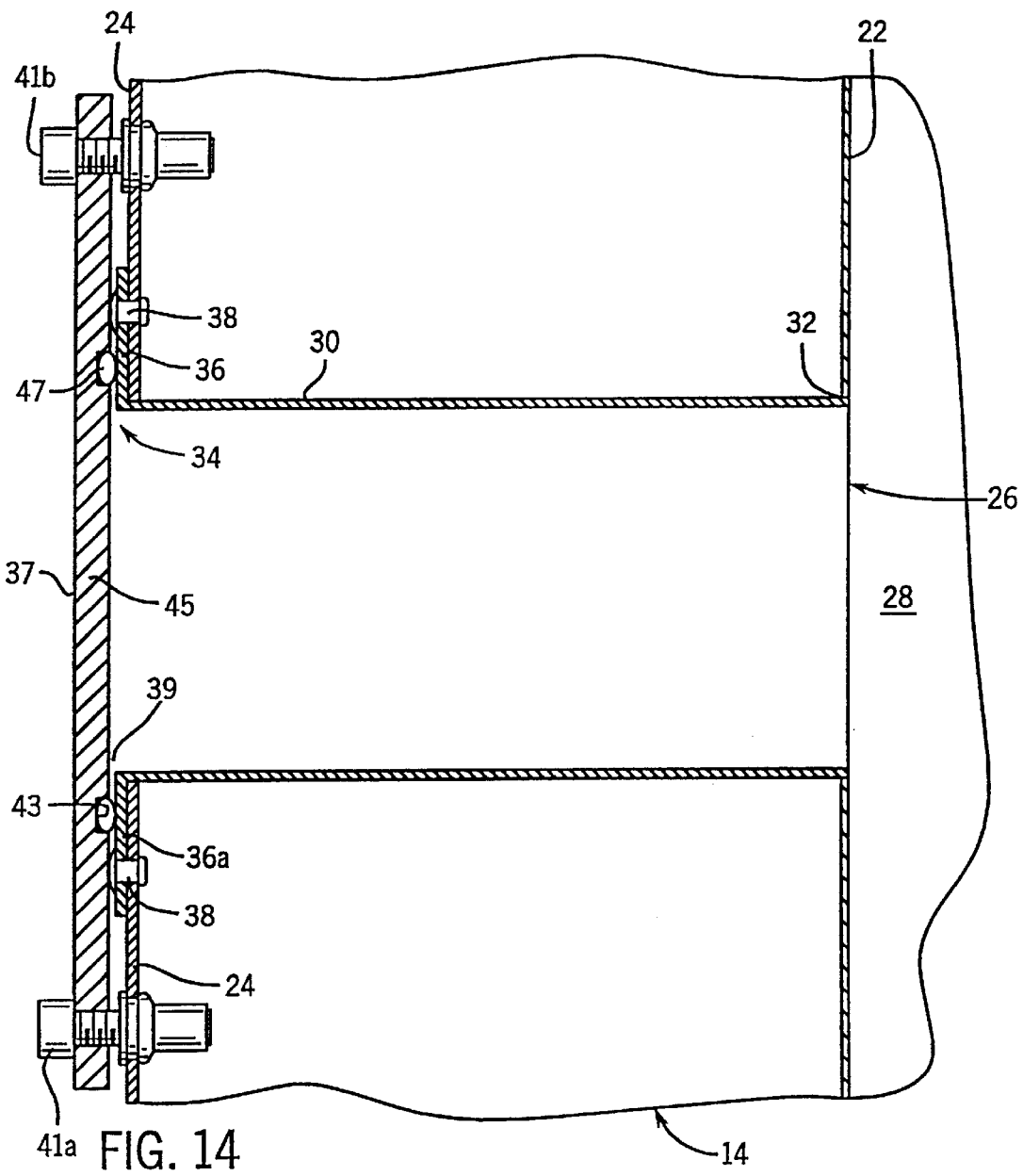
FIG. 14 is an enlarged, cross-sectional view showing an input port for the environmental testing chamber of the present invention.

Referring to FIG. 14, access port 26 in sidewall 14 is defined by generally cylindrical tube 30 having a first end 32 flush with inner panel 22 of sidewall 14 and a second, opposite end 34 having a flange 36 extending radially therefrom. Flange 36 is interconnected to outwardly directed surface 24a of outer panel 24 of sidewall 14 in any conventional manner, such as by rivets 38.

A sheet 37 formed from an electromagnetic and radio frequency wave absorbing material such as aluminum is positioned over opening 39 defined bye second end 34 of tube 30. Sheet 37 is interconnected to outer panel 24 of sidewall 14 by first and second fastening bolts 41a and 41b, respectively. A groove 43 may be formed in inwardly directed surface 45 of shield 37 for receiving a conductive gasket 47 therein. Conductive gasket 47 seals against the outer surface 36a of flange 36 so as to prevent the passage of electromagnetic and radio frequency waves therepast.

Figure 3:
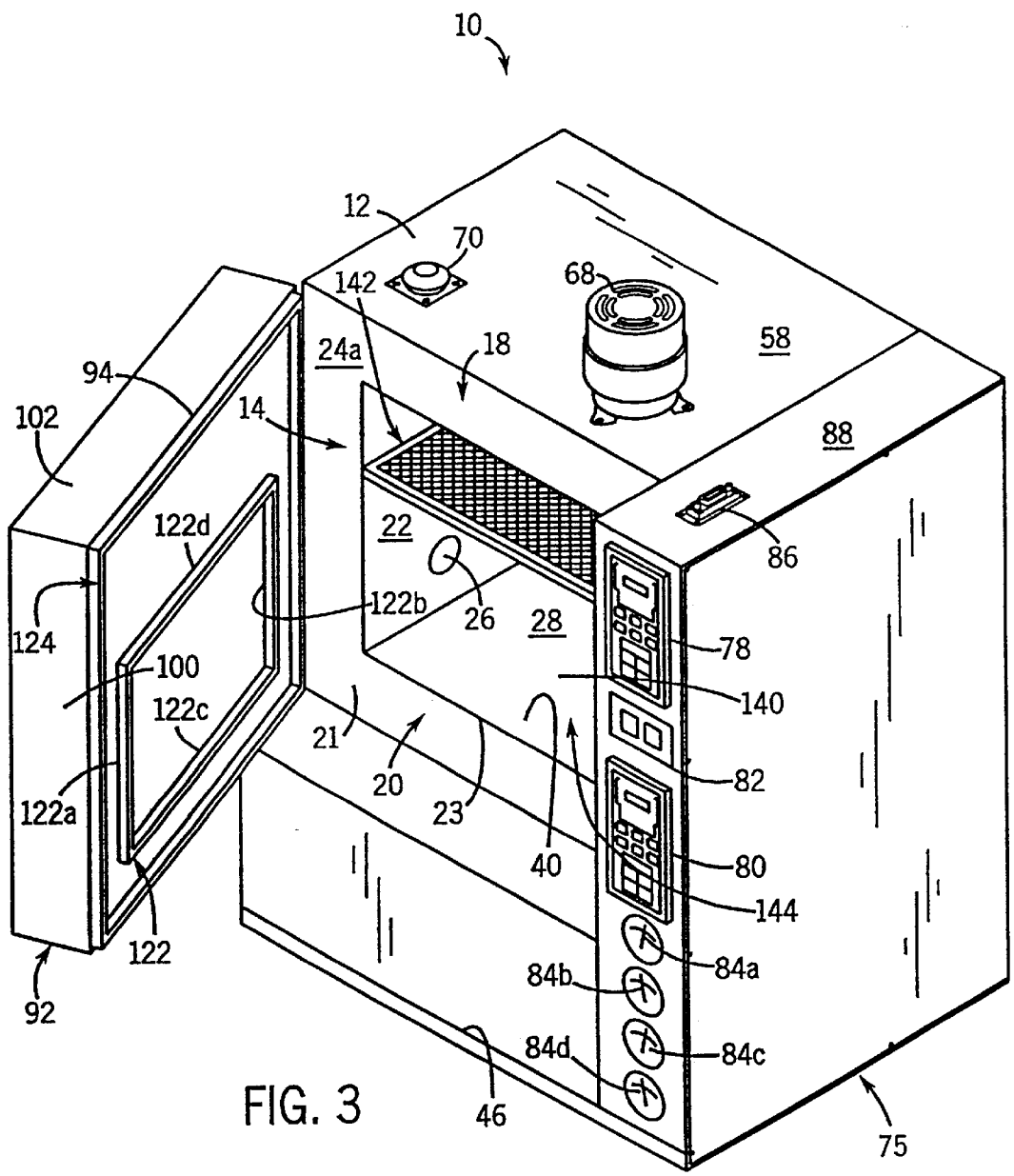
FIG. 3 is a front isometric view of the environmental testing chamber of FIG. 1 wherein the door thereof is in an open position.
Figure 4:
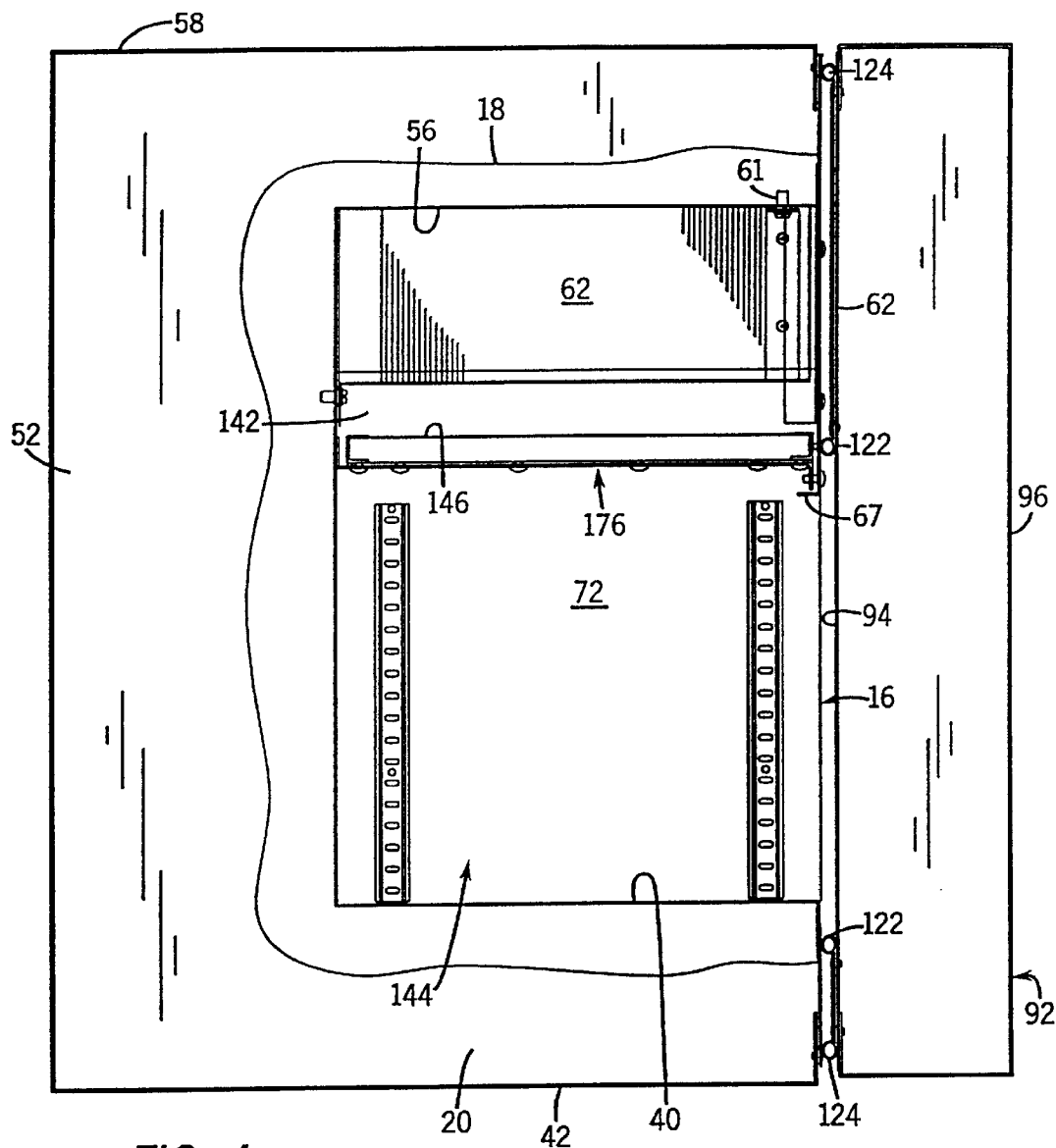
FIG. 4 is a side-elevational view, with portions broken away, showing the environmental testing chamber of the present invention.
Figure 5:
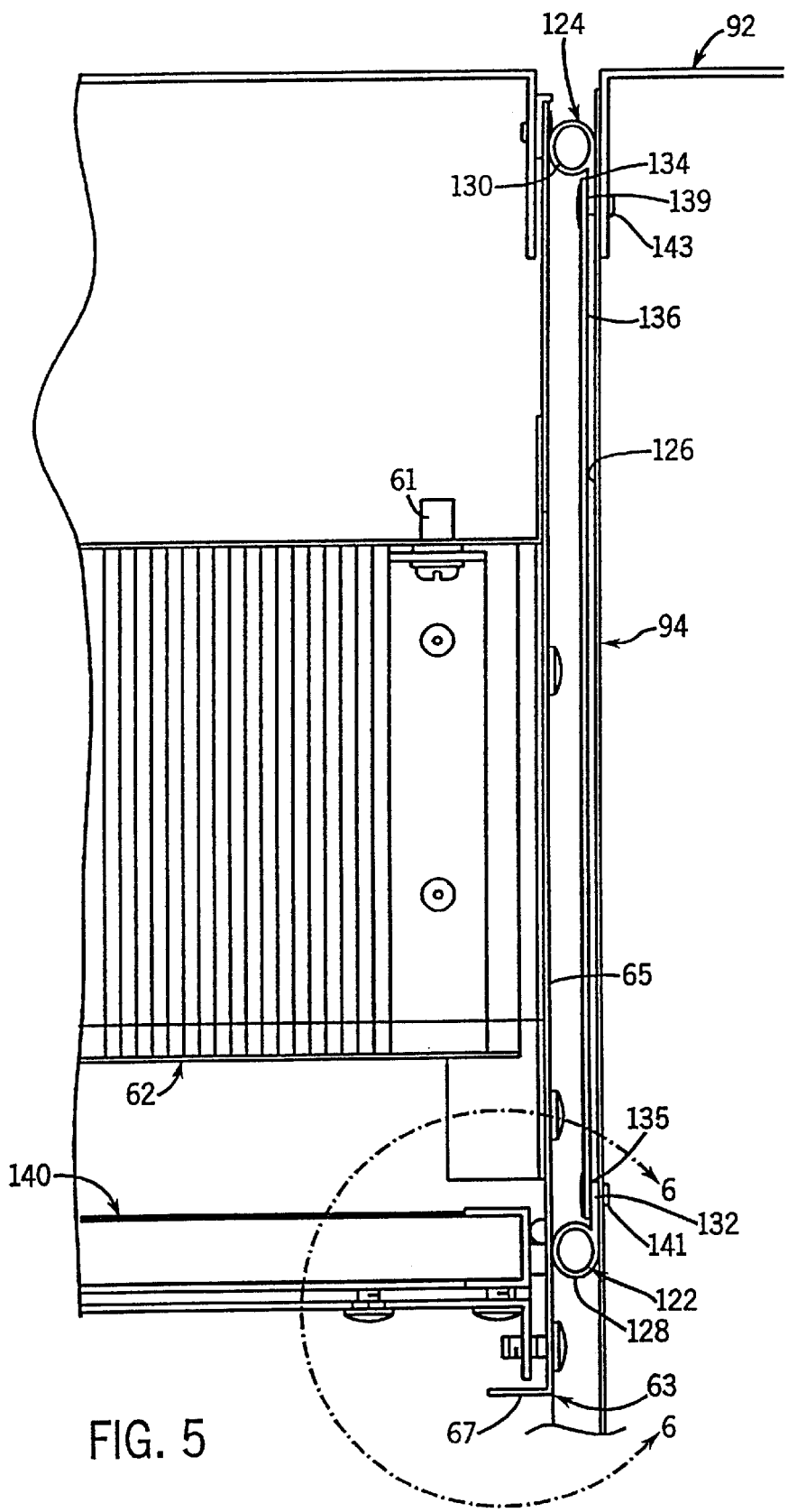
FIG. 5 is an enlarged, side-elevational view showing a portion of the environmental testing chamber of FIG. 4.
Figure 6:
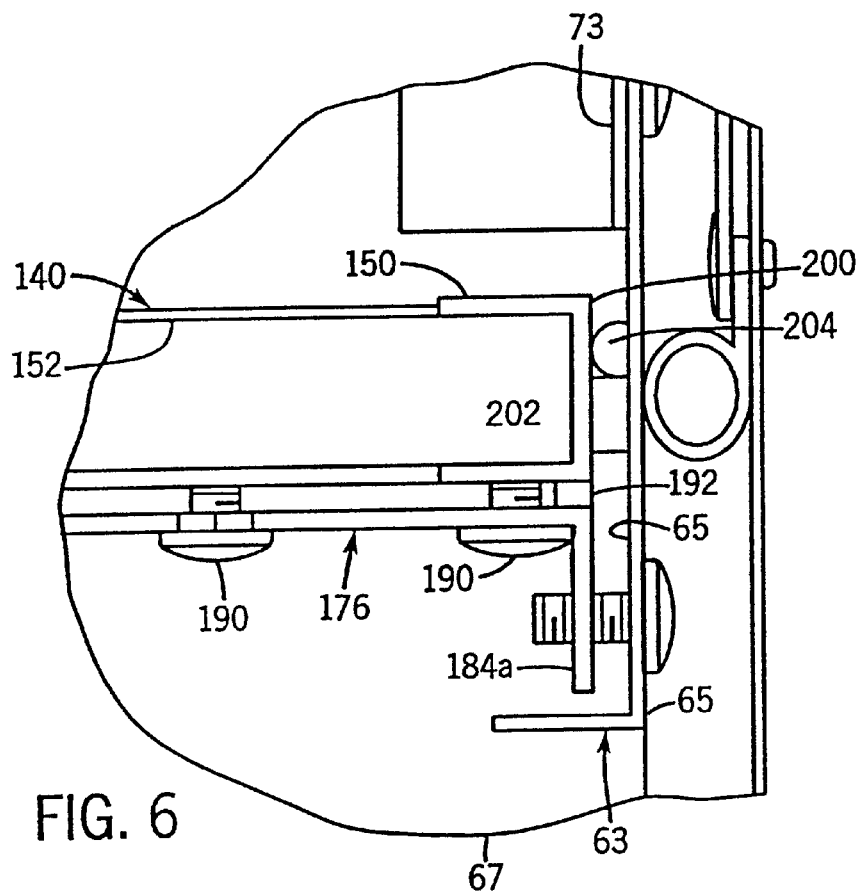
FIG. 6 is an enlarged, side-elevational view taking along line 6—6 of FIG. 5.

As best seen in FIG. 4, lower wall 20 of body portion 12 of environmental testing chamber 10 is defined by an inner panel 40 and an outer panel 42 having insulation disposed therebetween. It is contemplated that inner and outer panels 40 and 42, respectively, be formed from an electromagnetic and radio frequency wave absorbing material. It is further contemplated to mount outer panel 42 of lower wall 20 of body portion 12 on supporting base 46 so as to position body portion 12 of environmental testing chamber 10 above a supporting surface such as the floor of a laboratory, FIGS. 1–3. Supporting base 46 may include a plurality of vents 50, FIG. 2, to effectuate a heat exchange between the interior of supporting base 46 and the ambient air outside of environmental testing chamber 10.

Rear wall 22 of environmental testing chamber 10 is defined by an inner panel 52 and an outer panel 54 having insulation disposed therebetween. It is contemplated that inner and outer panels 52 and 54, respectively, be formed from an electromagnetic and radio frequency wave absorbing material. Base portion 12 further includes upper wall 18 projecting forward from rear wall 22. Upper wall 18 is defined by an inner panel 56 and an outer panel 58 having insulation disposed therebetween. It is contemplated that inner and outer panels 56 and 58, respectively, of upper wall 18 be formed from an electromagnetic and radio frequency wave absorbing material.

Figure 8:
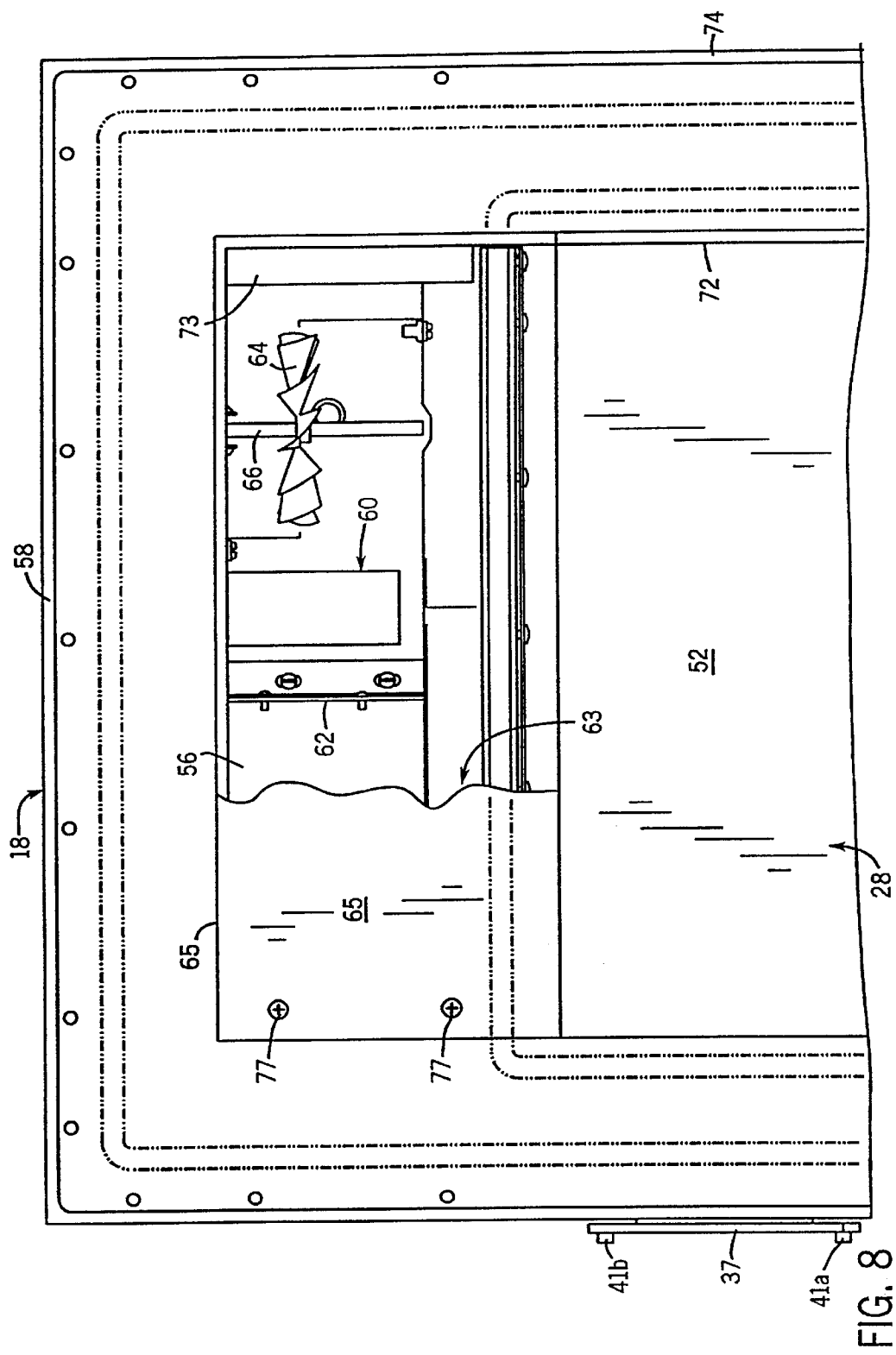
FIG. 8 is a front-elevational view, with portions broken away, showing exemplary climatic conditioning units for use in the environmental testing chamber of the present invention.

Referring to FIG. 8, it is contemplated to mount various climatic conditioning units to inner panel 56 of upper wall 18 of body portion 12. By way of example, a heater 60 may be mounted to inner panel 56 of upper wall 18 in order to heat interior cavity 28 of body portion 12. Similarly, an air conditioning unit 62 may be interconnected to inner panel 56 of upper wall 18 by bolt 61 in order to cool interior cavity 28 of body portion 12. A re-circulation fan 64 is mounted on shaft 66 of circulation motor 68, best seen in FIGS. 1–3. Circulation motor 68 is mounted to outer panel 58 of upper wall 18 and drives shaft 66 which extends through sidewall 18. As shaft 66 is driven by circulation motor 68, re-circulation fan 64 rotates therewith and re-circulates the air within interior chamber 28 of body portion 12.

An L-shaped cover plate 63 is positioned within opening 23 in body portion 12 so as to limit access to the various climatic conditioning units mounted to inner panel 58 of upper wall 18. First leg 65 of cover plate 63 abuts and is interconnected to inwardly directed flanges 73 extending into interior cavity 28 of body portion 12 from sidewalls 14 and 16, respectively, by a plurality of fastening screws 77. Second leg 67 of cover plate 63 extends from first leg 65 into interior cavity 28 of body portion 12. It is contemplated to provide a pressure relief vent 70 in outer panel 58 of upper wall 18 in order to prevent excessive air pressure within interior cavity 28 of body portion 12.

Sidewall 16 includes an inner panel 72 and an outer panel 74 having insulation disposed therebetween. It is contemplated that inner and outer panels 72 and 74, respectively, be formed from an electromagnetic and radio frequency wave absorbing material. A controller housing 75 is mounted to and abuts outer panel 74 of sidewall 16. Controller housing 75 houses a controller (not shown) for the heater 60 and air conditioning unit 62. A plurality of vents 79, FIG. 1, may be provided in controller housing 75 to effectuate a heat exchange between the interior of controller housing 75 and the ambient air outside of environmental testing chamber 10.

As best seen in FIGS. 1 and 3, controller housing 75 includes a forwardly directed face 76 having a plurality of user interface devices mounted thereto. By way of example, such user interface devices may include key pads 78 and 80 and function switches, collectively designated by the reference numeral 82. Key pads 78 and 80 and function switches 82 are interconnected to the controller (not shown) for heater 60 and air conditioning unit 62 in order to allow an operator to preset the climatic conditions within the interior cavity 28 of body portion 12 during testing. A plurality of analog gauges and/or dials 84*a*–*d* are mounted to forwardly directed face 76 of controller housing 75. Dials 84*a*–*d* may be interconnected to sensors (not shown) which measure pressures within the various climatic conditioning units in body portion 12.

Referring to FIG. 13, in order to monitor the temperature within interior cavity 28 of body portion 12, a thermocouple 81 is provided. Thermocouple 81 includes a pipe 83 having first and second opposite ends 83*a* and 83*b*, respectively. Pipe 83 extends through and is rigidly connected to inner panel 72 of sidewall 16 such that first end 83*a* of pipe 83 is received within interior cavity 28 of body portion 12 and second end 83*b* of pipe 83 is received within sidewall 16. First and second end caps 89*a* and 89*b*, respectively, are threaded on corresponding ends 83*a* and 83*b*, respectively, of pipe 83. A thermocouple wire 85 extends though first and second end caps 89*a* and 89*b*, respectively, of pipe 83 and through pipe 83 such that a first end is received in interior cavity 28 of body portion 12 and a second end is operatively connected to the controller (not shown). Thermocouple wire 85 is separated from the inner surface thereof by a plurality of plates 87 formed from a ferrite material. A shield 89 formed of electromagnetic and radio frequency wave absorbing material surrounds a portion of pipe 83 within interior cavity 28 of body portion 12.

As is conventional, when the portion of thermocouple wire 85 within interior cavity 28 of body portion 12 is heated, a corresponding direct current voltage appears thereacross such that the magnitude of the D.C. voltage corresponds to the temperature within interior cavity 28. It is contemplated that plates 87 and shield 89 limit any electromagnetic and radio frequency waves radiating from thermocouple wire 85 from entering interior cavity 28 of body portion 12.

Referring back to FIGS. 1–3, it is further contemplated to mount a computer interface 86 to upwardly directed face 88 of controller housing 75. Computer interface 86 is operatively connected to the controller (not shown) of heater 60 and air conditioning unit 62 thereby allowing a computer to be interconnected to the controller. Controller (not shown), heater 60, air conditioning unit 62, and circulation motor 68 may be interconnected to a power source (not shown) through power supply cord 90, FIG. 2.

Environmental testing chamber 10 further includes a door 92 having an inner panel 94 and an outer panel 96 having insulation disposed therebetween. It is contemplated that inner and outer panels 94 and 96, respectively, of door 92 be formed from an electromagnetic and radio frequency wave absorbing material. Inner panel 94 and outer panel 96 are interconnected by vertical sides 98 and 100 and upper and lower ends 102 and 104. Side 98 of door 92 is pivotably mounted to outer panel 24 of sidewall 14 of body portion 12 by first and second hinges 106 and 108, respectively, so as to allow door 92 to pivot thereon between a first closed position, FIG. 1, and a second open position, FIG. 3.

Figure 9:
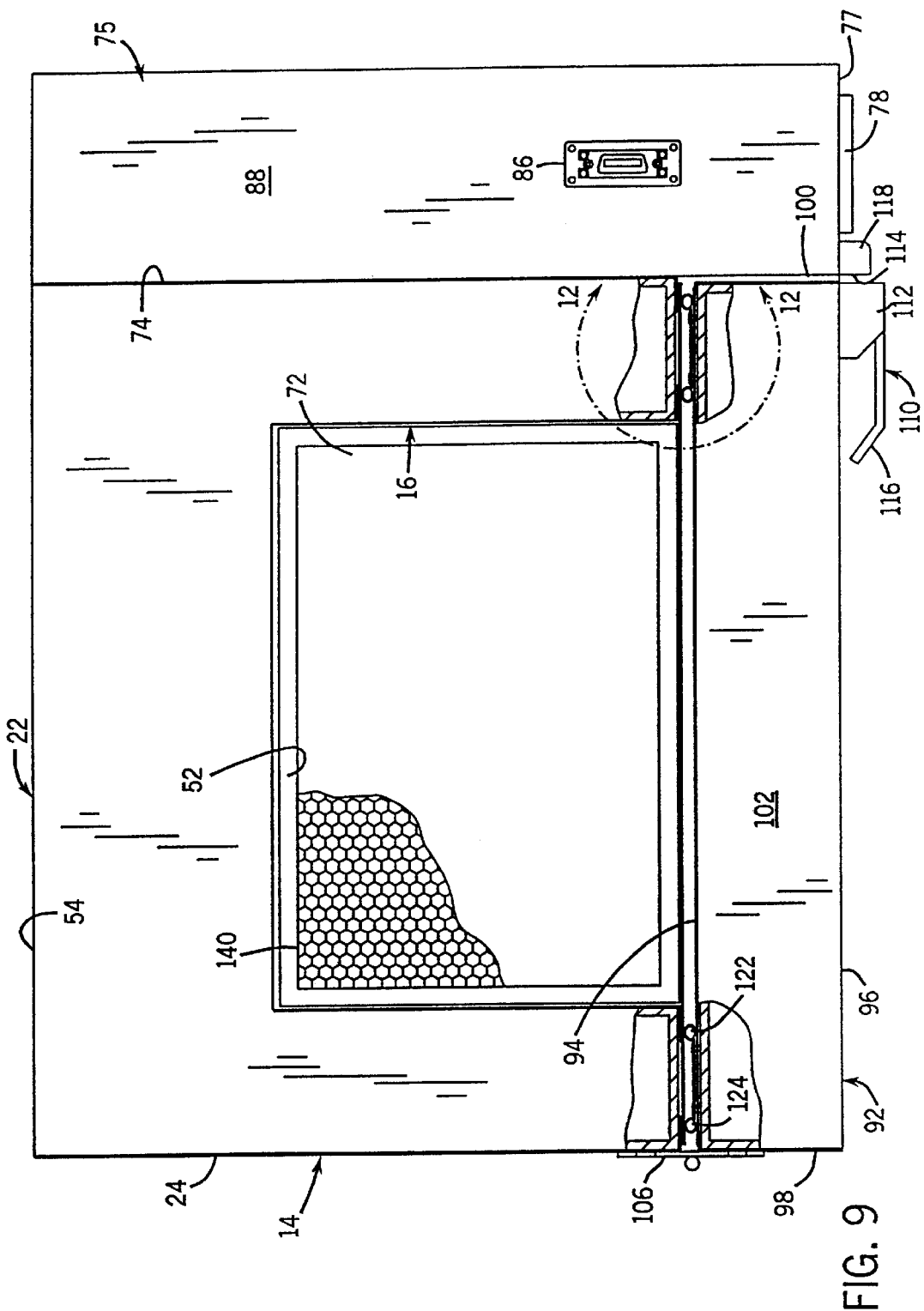
FIG. 9 is a top plan view, partially in section, showing the environmental testing chamber of the present invention.

A latch assembly 110 is provided to maintain door 92 in the closed position and to facilitate the opening of door 92. Latch assembly 110 includes a housing 112 having a bolt slideably received therein. Bolt 114 is movable a first retracted position wherein bolt 114 is received within housing 112, and a second extended position, FIG. 9, wherein bolt 114 extends from housing 112. Bolt 114 is biased toward the extended position such that when door 92 in the closed position, bolt 114 is receivable within a bolt receipt member 118 mounted to and extending from forwardly directed face 76 of controller housing 75. As is conventional, bolt 114 is movable between the retracted and the extended position in response to pivoting of handle 116.

As best seen at FIGS. 3–6, and 12, inner and outer conductive gaskets 122 and 124, respectively, are mounted to the inwardly directed surface 126 of inner panel 94. Inner and outer conductive gaskets 122 and 124, respectively, include resilient tubular portions 128 and 130, respectively, and corresponding attachment flanges 132 and 134, respectively, extending therefrom. Attachment flange 132 of conductive gasket 122 and conductive flange 134 of conductive gasket 124 are directed towards each other and abut inwardly directed surface 126 of inner panel 94 of door 92. A mounting plate 136 extends between inner and outer conductive gaskets 122 and 124 such that inner portion 138 of mounting plate 136 overlaps attachment flange 132 of conductive gasket 122 and such the outer peripheral edge 139 of mounting plate 136 overlaps attachment flange 134 of outer conductive gasket 124. Attachment elements, such as rivets 141 and 143, extend through mounting plate 136 and corresponding attachment flanges 132 and 134 of inner and outer conductive gaskets 122 and 124, respectively, in order to secure inner and outer conductive gaskets 122 and 124, respectively, to inner panel 94 of door 92.

As best seen in FIGS. 4–6 and 12, with door 92 in the door closed position, outer conductive gasket 124 abuts outwardly directed face 21*a* of face plate 21 so as to form a seal between door 92 and face plate 21 of body portion 12 thereby preventing the passage of electromagnetic and radio frequency waves into or out of interior cavity 28 of body portion 12 of environmental testing chamber 10. Similarly, sides 122*a* and 122*b* of inner conductive gasket 122 and bottom 122*c* of inner conductive gasket 122 abut outwardly directed face 21*a* of face plate 21. However, top 122*d* of inner conductive gasket 122 engages the outer surface 65*b* of first leg 65 of cover plate 63. As a result, inner conductive gasket 122 forms a seal between door 92, face plate 21, and cover plate 63 so as to further prevent the passage of electromagnetic and radio frequency waves into or out of interior cavity 28 of body portion 12 of environmental testing chamber 10.

Figure 7:
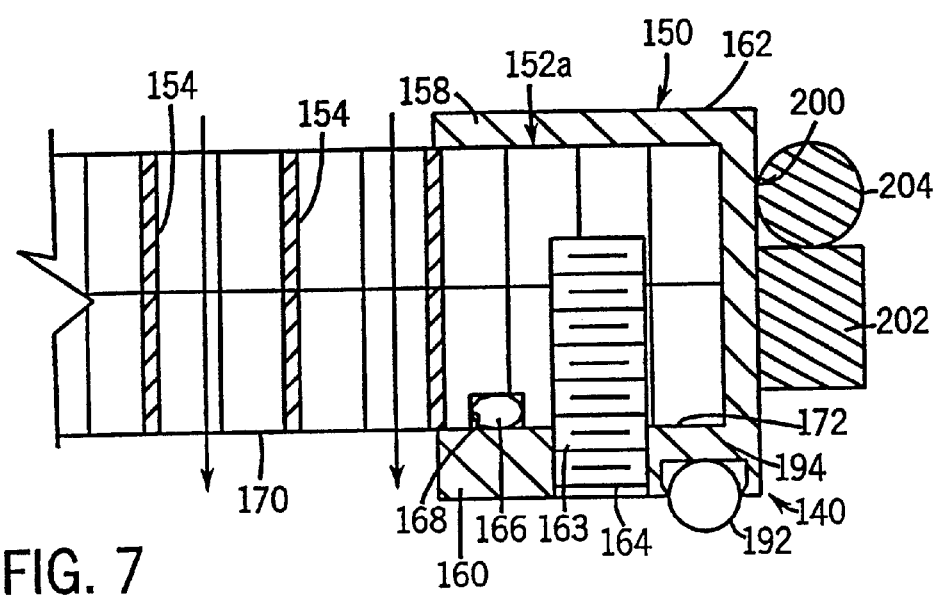
FIG. 7 is an enlarged, cross-sectional view of a portion of a shield for the environmental testing chamber of FIG. 6.
Figure 10:
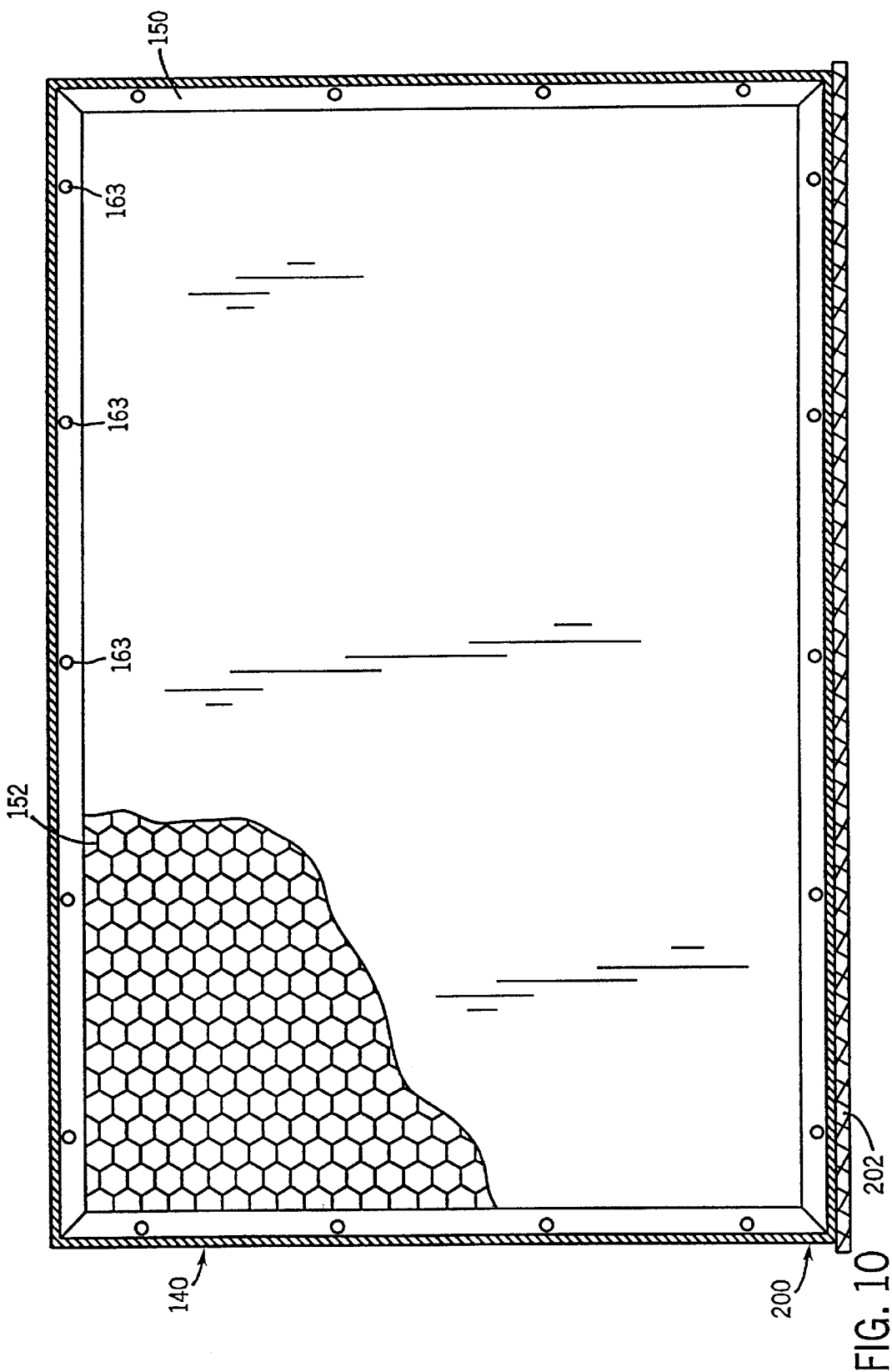
FIG. 10 is an enlarged, bottom plan view showing the electromagnetic and radio frequency shield for the environmental testing chamber of the present invention.
Figure 11:
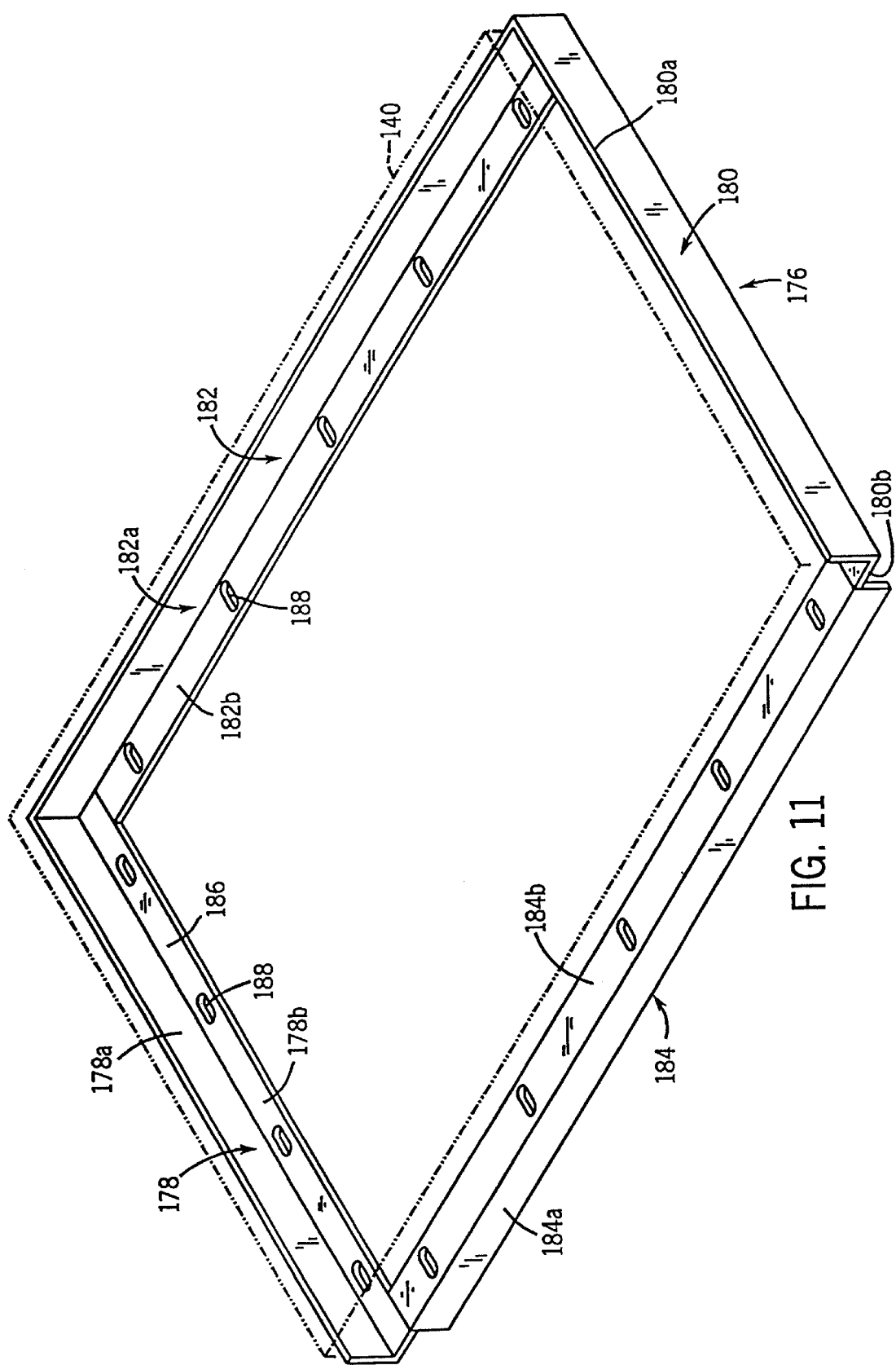
FIG. 11 is a isometric view of a mounting bracket for the electromagnetic and radio frequency shield which is mounted within the interior cavity of the environmental testing chamber of the present invention.

In order to prevent the passage of electromagnetic and radio frequency waves between the devices or products 25 being tested and the climatic conditioning units interconnected to inner panel 56 of upper wall 18, as heretofore described, a barrier or screen 140 is positioned therebetween so as to divide interior cavity 28 into an environmental conditioning section 142 and a testing section 144. Referring to FIGS. 7 and 10, screen 140 includes a generally rectangular frame 150 for supporting a sheet 152 of electromagnetic and radio frequency wave absorbing material having a honeycomb configuration. It is contemplated to construct sheet 152 from a material such as aluminum. As best seen in FIG. 7, openings 154 in sheet 152 allow for the passage of air therethrough such that by rotation of re-circulation fan 64 by circulation motor 68, the air conditioned by the climatic conditioning units in the environmental conditioning section 142 of interior cavity 28 in body portion 12 may flow through openings 154 in sheet 152 and into the testing section 144 of interior cavity 28 of body portion 12, and vice versa, thereby maximizing the effectiveness of climatic conditioning units of environmental testing chamber 10.

Outer peripheral end 152a of sheet 152 is received within a channel 156 in frame 150. Channel 156 has a generally C-shaped cross-section having a dimension generally equal to the width of sheet 152. Channel 156 of frame 150 is defined by generally horizontal upper and lower frame elements 158 and 160, respectively, which are spaced by a vertical frame wall 162. Lower frame element 160 includes a plurality of circumferentially spaced threaded apertures 163 for receiving threaded inserts 164 therein. The threaded inserts 164 are threaded into threaded apertures 163 in lower frame element 160 and into the outer peripheral end 152a of sheet 152 so as to interconnect frame 150 and sheet 152.

In order to insure a proper fit between outer peripheral edge 152a of sheet 152 within C-shaped cavity 156 of frame 150, a sealing element 166 is positioned within a recess 168 formed in the lower surface 170 of sheet 152. Sealing element 162 engages inwardly directed surface 172 of lower frame element 160 so as to prevent the passage of electromagnetic and radio frequency waves therepast.

Frame 150, and hence sheet 152, is supported within interior cavity 28 in body portion 12 by a support member 176. Support member 176 includes first and second generally L-shaped elongated side brackets 178 and 180, respectively, interconnected by an elongated generally L-shaped rear bracket 182 perpendicular thereto. Vertical legs 178a and 180a of side brackets 178 and 180, respectively, are interconnected to corresponding inner panels 22 and 72 of sidewalls 14 and 16, respectively. Vertical leg 182a of rear bracket 182 is interconnected to inner panel 52 of rear wall 22.

Side brackets 178 and 180 further include horizontal legs 178b and 180b, respectively, which extend toward each other. Horizontal legs 178b and 180b of side brackets 178 and 180, respectively, are interconnected by horizontal leg 182b of rear bracket 182 and horizontal leg 184b of an elongated, generally L-shaped front bracket 184 which is generally parallel to rear bracket 182. Horizontal legs 178b and 180b of side brackets 178 and 180, respectively, and horizontal legs 182b and 184b of rear and front brackets 182 and 184, respectively, define a supporting surface designated by the reference numeral 186 for supporting screen 140 thereon.

Supporting surface 186 includes a plurality of circumferentially spaced oblong apertures 188 therein. Oblong apertures 188 are aligned with corresponding apertures in frame 150 of screen 140 thereby allowing threaded inserts 164 to be threaded through corresponding oblong apertures 188 in support surface 186 and into lower frame element 160 of frame 150 to interconnect screen 140 and support member 176.

Due to the oblong configuration of oblong apertures 188 in supporting surface 186 of supporting member 176, the position of screen 140 with respect to support member 176 may be adjusted forwardly or rearwardly to desired location for reasons hereinafter described. A seal 192 is seated within a corresponding recess 194 in lower frame element 160 of frame 150. With screen 140 interconnected to supporting member 176, seal 192 engages supporting surface 186 so as to prevent the passage of electromagnetic and radio frequency waves therepast.

Front bracket 184 of supporting member 76 includes a vertical leg 184a which depends from horizontal leg 184b thereof. Vertical leg 184a of front bracket 184 is generally parallel to first leg 65 of cover plate 63 and is interconnected thereto by a plurality of bolts 196 spaced along the entire length of vertical leg 184a of front bracket 184. In order to prevent the passage of electromagnetic and radio frequency waves between first leg 65 of cover plate 63 and the forward end 200 of frame 150 of shield 140, a gasket support 202 is affixed to the entire length of the forward end 200 of frame 150 of screen 140. Conductive gasket 204 is positioned upon gasket support 202 along the entire length of the forward end 200 of frame 150. The position of screen 140 with respect to support member 176 may be adjusted as heretofore described in order that conductive gasket 204 forms a seal between inner surface 65a of first leg 65 of cover plate 63 and forward end 200 of support frame 150 of shield 140 so as to prevent the passage of electromagnetic and radio frequency waves therepast.

Figure 15:
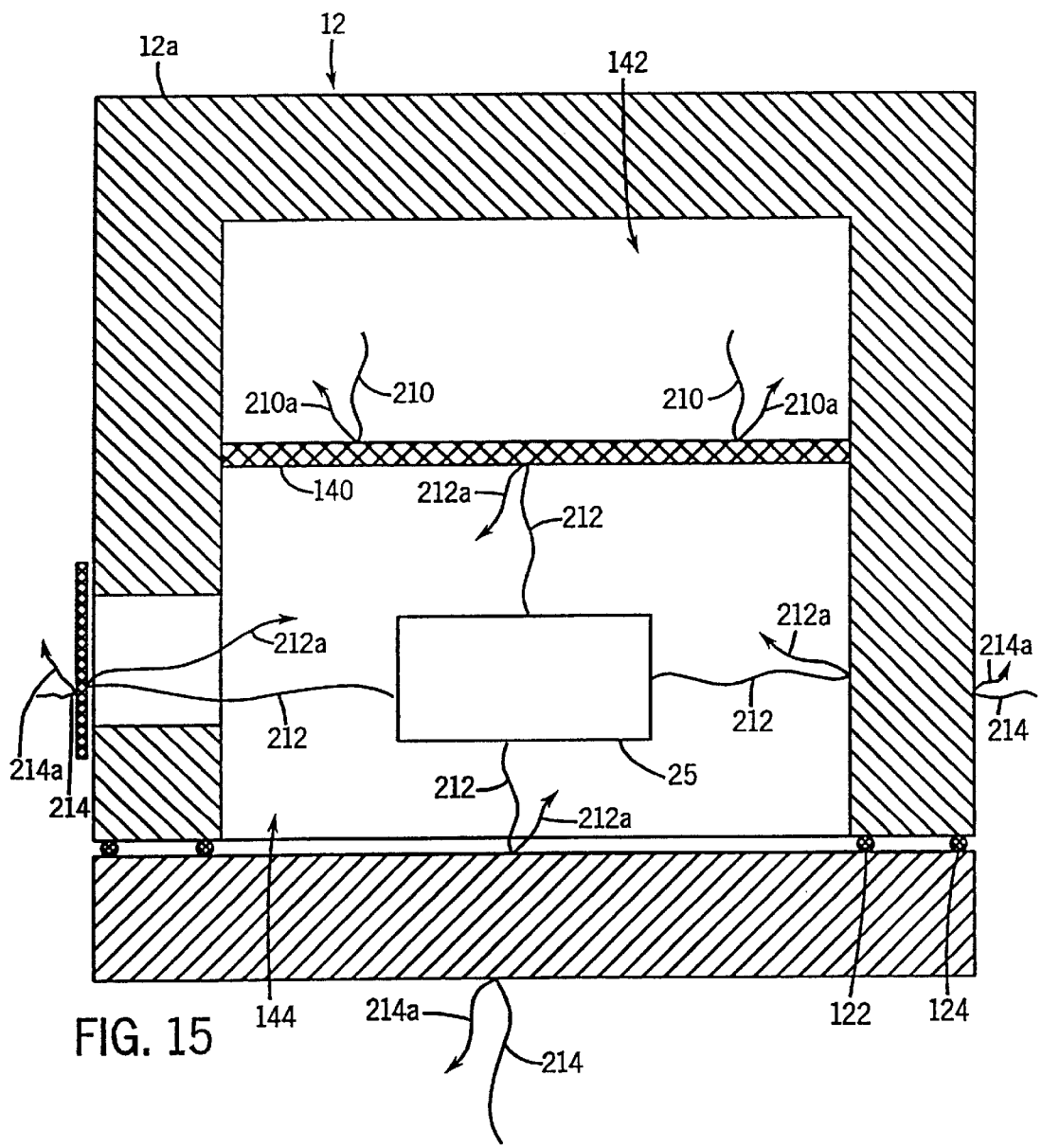
FIG. 15 is a cross-sectional view of showing a first alternate embodiment of the environmental testing chamber of the present invention.

Referring to FIG. 15, a schematic of an alternate embodiment of environmental testing chamber 10 is shown. In such alternate embodiment, the climatic conditioning units are mounted to inner panel of rear wall 22. As such, screen 140 is positioned vertically within interior cavity 28 of body portion 12 such that the environmental conditioning section 142 of interior cavity 28 is provided at the rear of body portion 12 and the testing section 144 of interior cavity 28 is provided at the forward end of interior cavity 28 of body portion 12. The remaining aspects of the environmental testing chamber 144 shown in FIG. 15 are identical to those heretofore described such that the previous description of environmental testing chamber 10 is understood to describe the environmental testing chamber shown in FIG. 15.

In operation, product 25 is positioned within the testing portion 144 of interior cavity 28 in body portion 12. Electromagnetic and radio frequency waves designated by the reference numeral 210 generated by the climatic conditioning units in the environmental conditioning section 142 of interior cavity 28 of body portion 12 are either absorbed by sheet 152 of screen 140 or are reflected away from testing portion 144. The reflected portion 210a of electromagnetic and radio frequency waves 210 continue to be reflected until absorbed by sheet 152 of screen 140 or by the portions of the inner panels of body portion 12 which communicate with the environmental conditioning section 142 of body portion 12.

Similarly, the electromagnetic and radio frequency waves 212 generated by product 25 are either absorbed by sheet 152 of screen 140, sheet 37 overlapping opening 39 to access port 26 and/or portions of the inner panels of body portion 12 which are in communication with testing section 144 of interior cavity 28 of body portion 12. The reflected portions 212a of electromagnetic and radio frequency waves 212 continue to be reflected until completely absorbed.

With respect to electromagnetic and radio frequency waves 214 from outside environmental testing chamber 10, such waves 214 are either absorbed or reflected by the outer panels which define the outer surface 12a of body portion 12 and/or sheet 37. The reflected portions 214a of electromagnetic and radio frequency waves 214 are harmlessly directed away from the testing section 144 of interior cavity 28 of environmental testing chamber 10.

Figure 16:
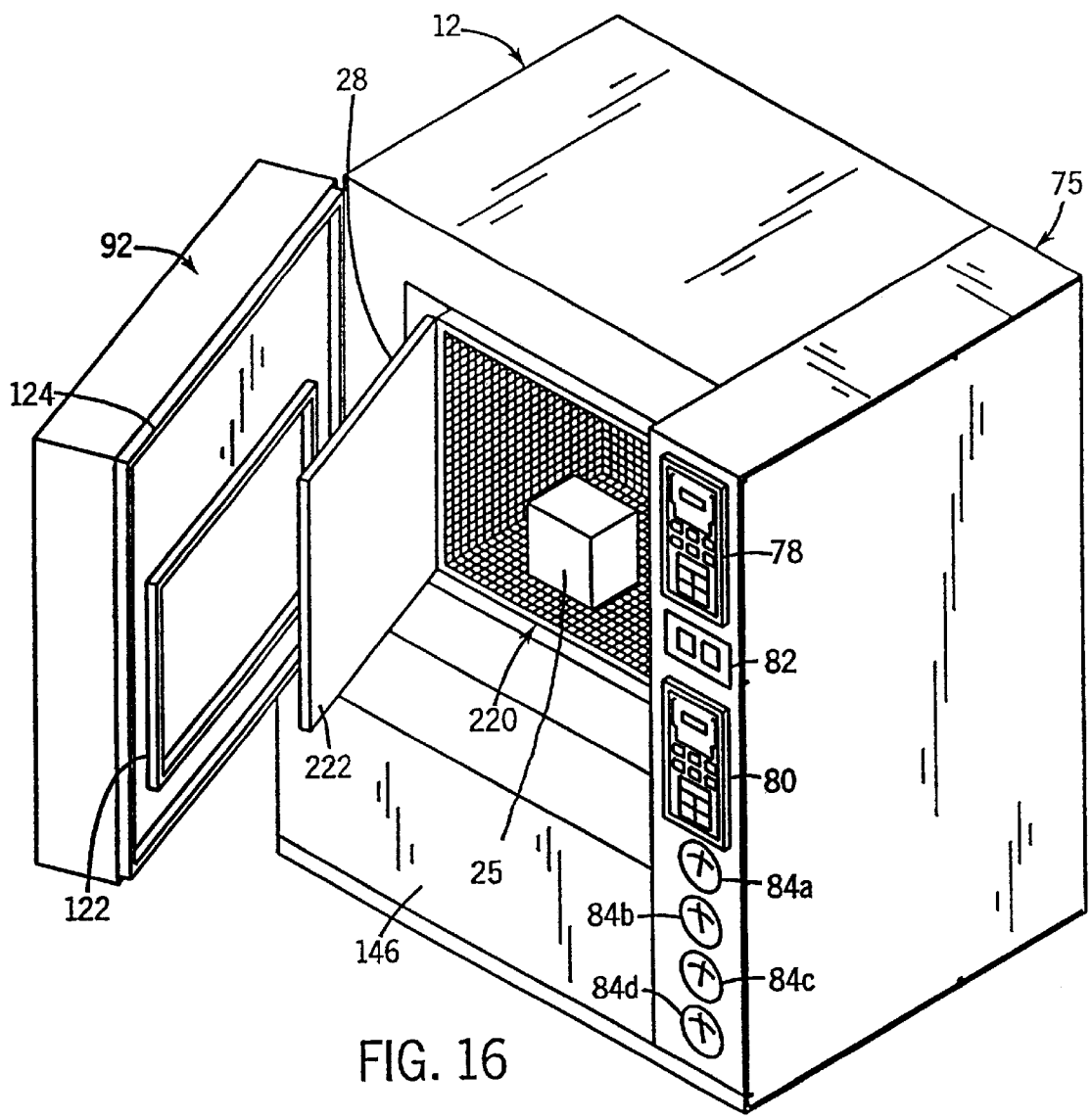
FIG. 16 is a front, isometric view of a second alternate embodiment of the environmental testing chamber of the present invention.

Referring to FIG. 16, a still further embodiment of environmental testing chamber 10 is shown. A box generally designated by the reference numeral 220 is provided for receipt within interior cavity 28 of body portion 12. Box 220 is formed from electromagnetic and radio frequency wave absorbing material having a honeycomb configuration and includes a door 222 pivotable between a first open position, FIG. 16, which allows an operator to place product 25 or remove product 25 from the interior of box 220 and a closed position (not shown) wherein product 25 is entirely enclosed by electromagnetic and radio frequency wave absorbing material. The remaining aspects of the environmental testing chamber shown in FIG. 16 are identical to those heretofore described with respect to the prior embodiments such that the previous descriptions of environmental testing chamber 10 is understood to describe the environmental testing chamber shown in FIG. 16. It can be readily understood that the alternate embodiment disclosed in FIG. 16 will prevent the passage of electromagnetic and radio frequency waves between the interior of box 220 and the exterior thereof.

Various modes of carrying out the invention are contemplated as being within the scope of the following claims particularly pointing out and distinctly claiming the subject matter which is regarded as the invention.

We claim:

1. An apparatus for conducting environmental tests on a device, comprising:
   a cabinet defining a testing chamber for receiving the device therein;
   a climatic conditioning unit for producing desired climatic conditions in the testing chamber;
   isolation structure for isolating the device from the climatic conditioning unit and limiting the passage of predetermined waves therebetween; and
   a thermocouple extending into the testing chamber for monitoring the temperature therein, the thermocouple partially surrounded by an isolation tube to limit interference generated by the thermocouple from entering the testing chamber, the isolation tube including a first inner layer for preventing electromagnetic waves from passing therethrough and a second outer layer.

2. The apparatus of claim 1 wherein the isolation structure includes a screen enclosure surrounding the device, the screen enclosure receivable within the testing chamber.

3. The apparatus of claim 2 wherein the enclosure is formed from an electromagnetic wave absorbing material.

4. The apparatus of claim 2 wherein the enclosure is formed from a radio wave absorbing material.

5. The apparatus of claim 2 wherein the enclosure includes a plurality of openings therein to allow for the flow of air therethrough.

6. The apparatus of claim 1 wherein the isolation structure includes a shield positioned between the climatic conditioning unit and the device.

7. The apparatus of claim 1 wherein the inner layer is formed from a plurality of ferrite segments.

8. An apparatus for conducting environmental tests on a device, comprising:
   a cabinet defining a testing chamber for receiving the device therein;
   a door pivotably mounted to the cabinet and movable between a first open position allowing access to the testing chamber and a second closed position preventing access to the testing chamber;
   door sealing structure for sealing the intersection of the door and the cabinet when the door is in the closed position;
   a climatic conditioning unit for producing desired climatic conditions in the testing chamber; and
   isolation structure for isolating the device from the climatic conditioning unit, the isolation structure limiting predetermined waves from passing therethrough and including a shield positioned within the testing chamber between the climatic conditioning unit and the device, the shield including a screen portion.

9. The apparatus of claim 8 further comprising a thermocouple extending into the testing chamber for monitoring the temperature therein, the thermocouple partially surrounded by an isolation tube to limit interference generated by the thermocouple from entering the testing chamber.

10. The apparatus of claim 8 wherein the shield surrounds the device.

11. The apparatus of claim 8 wherein the shield is formed from an electromagnetic wave absorbing material.

12. The apparatus of claim 8 wherein the shield is formed from a radio wave absorbing material.

13. The apparatus of claim 8 wherein the shield is positioned within the testing chamber, the shield dividing testing chamber into a first section for receiving the climatic conditioning unit therein and a second section for receiving the device therein.

14. The apparatus of claim 13 further comprising a shield sealing structure extending about a portion of the outer periphery of the shield, the shield sealing structure preventing the passage of electromagnetic and radio wavestherepast.

15. An apparatus for conducting environmental tests on a device, comprising:
   a cabinet defining a testing chamber for receiving the device therein;
   a door pivotably mounted to the cabinet and movable between a first open position allowing access to the testing chamber and a second closed position preventing access to the testing chamber;
   door sealing structure for sealing the intersection of the door and the cabinet when the door is in the closed position;
   a climatic conditioning unit for producing desired climatic conditions in the testing chamber;
   isolation structure for isolating the device from the climatic conditioning unit, the isolation structure limiting predetermined waves from passing therethrough and including a shield positioned within the testing chamber between the climatic conditioning unit and the device, the shield including a plurality of passages arranged in a honeycomb configuration which allow for the flow of air therethrough.

16. The apparatus of claim 15 wherein the shield is formed from an electromagnetic wave absorbing material.

17. The apparatus of claim 15 wherein the shield is formed from a radio wave absorbing material.

18. The apparatus of claim 15 wherein the shield includes a plurality of openings therein so to allow for the flow of air therethrough.

19. The apparatus of claim 15 wherein the shield includes a screen portion.

20. The apparatus of claim 15 wherein the shield divides the testing chamber into a first section for receiving the climatic conditioning unit therein and a second section for receiving the device therein.

21. The apparatus of claim 20 further comprising a shield sealing structure extending about a portion of the outer periphery of the shield, the shield sealing structure preventing the passage of electromagnetic and radio waves therepast.

\* \* \* \* \*